United States Patent
Newman (10) Patent No.: US 6,371,355 B1
(45) Date of Patent: Apr. 16, 2002

(54) METHOD AND APPARATUS FOR SOLDER JOINT INTEGRITY ASSESSMENT

(75) Inventor: Keith G. Newman, Sunnyvale, CA (US)

(73) Assignee: Sun Microsystems, Inc., Palo Alto, CA (US)

( * ) Notice: Subject to any disclaimer, the term of this patent is extended or adjusted under 35 U.S.C. 154(b) by 0 days.

(21) Appl. No.: 09/648,500

(22) Filed: Aug. 25, 2000

(51) Int. Cl.[7] .......................... B23K 31/12; B23K 5/00; B23K 31/00; F27D 11/00
(52) U.S. Cl. .................... 228/103; 228/102; 228/180.5; 219/388; 219/391
(58) Field of Search ................................. 228/102, 103, 228/180.5; 219/388, 391

(56) References Cited

U.S. PATENT DOCUMENTS

| | | | | |
|---|---|---|---|---|
| 4,287,766 A | * | 9/1981 | Ensminger .................... 73/582 |
| 4,878,611 A | * | 11/1989 | LoVasco et al. .......... 228/180.2 |
| 5,145,104 A | * | 9/1992 | Apap et al. .................. 228/179 |
| 5,380,559 A | * | 1/1995 | Filas et al. ................... 427/305 |
| 5,471,092 A | * | 11/1995 | Chan et al. .................. 257/753 |
| 5,493,775 A | * | 2/1996 | Darekar et al. ................ 29/840 |
| 5,535,006 A | * | 7/1996 | Telschow et al. ............. 356/394 |
| 5,651,493 A | * | 7/1997 | Bielick et al. ............... 228/105 |
| 5,736,646 A | * | 4/1998 | Dickinson et al. ............. 73/814 |
| 5,928,458 A | * | 7/1999 | Aschenbrenner et al. 156/307.1 |
| 6,138,893 A | * | 10/2000 | Caletka et al. .............. 228/102 |

\* cited by examiner

*Primary Examiner*—Tom Dunn
*Assistant Examiner*—Zidia Pittman
(74) *Attorney, Agent, or Firm*—J. D. Harriman II, Esq.; Coudert Brothers LLP (57) ABSTRACT

The present invention is a method for solder joint integrity assessment. The invention comprises collecting data from one or more solder joint strain tests and characterizing the solder joint data integrity using a force-deflection graph. A force-deflection graph characterizes the response force of a solder joint to applied strain as a function of time. One embodiment of the invention uses the slope of the graph to characterize the integrity of the solder joint. Another embodiment uses the area below the graph to characterize the integrity of the solder joint. To generate the force-deflection graph, the invention applies one or more tests to the solder joint. In one embodiment, a shear test is applied to the solder joint. In another embodiment, a cold pull test is applied to the solder joint. In another embodiment, a hot pull test is applied to the solder joint.

7 Claims, 14 Drawing Sheets

Solder Joint Characterization in Accordance with One Embodiment of the Present Invention Figure 1A: Developing Crack in Solder Material

Figure 1B: Shear Test

Figure 1C: General Purpose Computer Architecture

Figure 2: Cold Pull Test

Figure 3: Hot Pull Test

Figure 4: Solder Joint Characterization in Accordance with One Embodiment of the Present Invention

Figure 5: Gathering Solder Joint Integrity Data

Figure 6: Force-Deflection Graph

Figure 7: Recording Solder Joint Integrity Data

Figure 8A: Force-Deflection Curve

Figure 8B: Force-Deflection Curve

Figure 8C: Area Beneath Force-Deflection Curve

Figure 8D: Area Beneath Force-Deflection Curve

Figure 9: Characterizing Solder Joint Integrity Data

METHOD AND APPARATUS FOR SOLDER JOINT INTEGRITY ASSESSMENT

BACKGROUND OF THE INVENTION

1. Field of the Invention

The present invention relates to electronic circuits, and specifically to a method and apparatus for assessment of the integrity of a solder joint.

2. Background Art

In some electronic systems, components are coupled by "soldering" the components directly to a board. Soldering is the act of heating two metals and a solder alloy to form a "solder joint." As the solder joint cools, an electrical and mechanical connection is formed. The reliability of the electronic systems depends in part on the integrity of its solder joints. Thus, it is desirable to characterize the integrity of solder joints so that solder joint behavior can be accurately predicted during manufacture and use.

The Soldering Process

The basic operational steps of soldering are as follows: (1) thorough cleaning of the metal to be joined by abrasive or chemical means; (2) application of a flux to remove oxides on heating and promote spreading and wetting of the solder; (3) alignment of parts to produce a controlled gap of 0.025 to 0.125 mm (0.001 to 0.005 inch); (4) application of heat; (5) feeding solder to the joint; (6) cooling without movement; and (7) removal of corrosive flux residues.

Solder is formed from a variety of metals. For example, tin, lead, silver, bismuth, indium, antimony and cadmium are frequently used in forming solder. Lead-tin alloy solders are widely used in the electrical industry. Solders are supplied in wire, bar, or premixed-paste form, depending on the application. Electronic circuits require a noncorrosive flux; fluxes based on rosin using alcohol as a carrier are sufficiently active to produce a good bond.

Soldering can be carried out using various heating methods, including, for example, conduction, infrared, vapor phase, hot gas, convection, induction, resistance and laser. Each method has its merits in cost, performance or operational convenience. For localized fast heating, laser offers the best performance followed by hot air. For uniform temperature, vapor phase is the best method. For versatility, volume and economy, convection and infrared are appropriate choices. Wave-soldering devices are prominent in printed-circuit production.

Solder Joint Failure

Solder joint failure often results when cracks form in the solder material because of a strain. In a lead-tin alloy solder joint, the solder joint deforms non-uniformly, with deformations forming primarily along the edges where the softest solder material is located. The lead-tin alloy in the deformations recrystallizes, and the recrystallized material is soft compared to the surrounding solder material. Further strain causes deformations near the recrystallized solder material, and the new deformations also recrystallize, thus extending the region of softer material. Continued strain results in cracks forming in the region of softer material. Ultimately, the cracks extend through the entire solder material, causing the solder joint to fail.

Figure 1A:
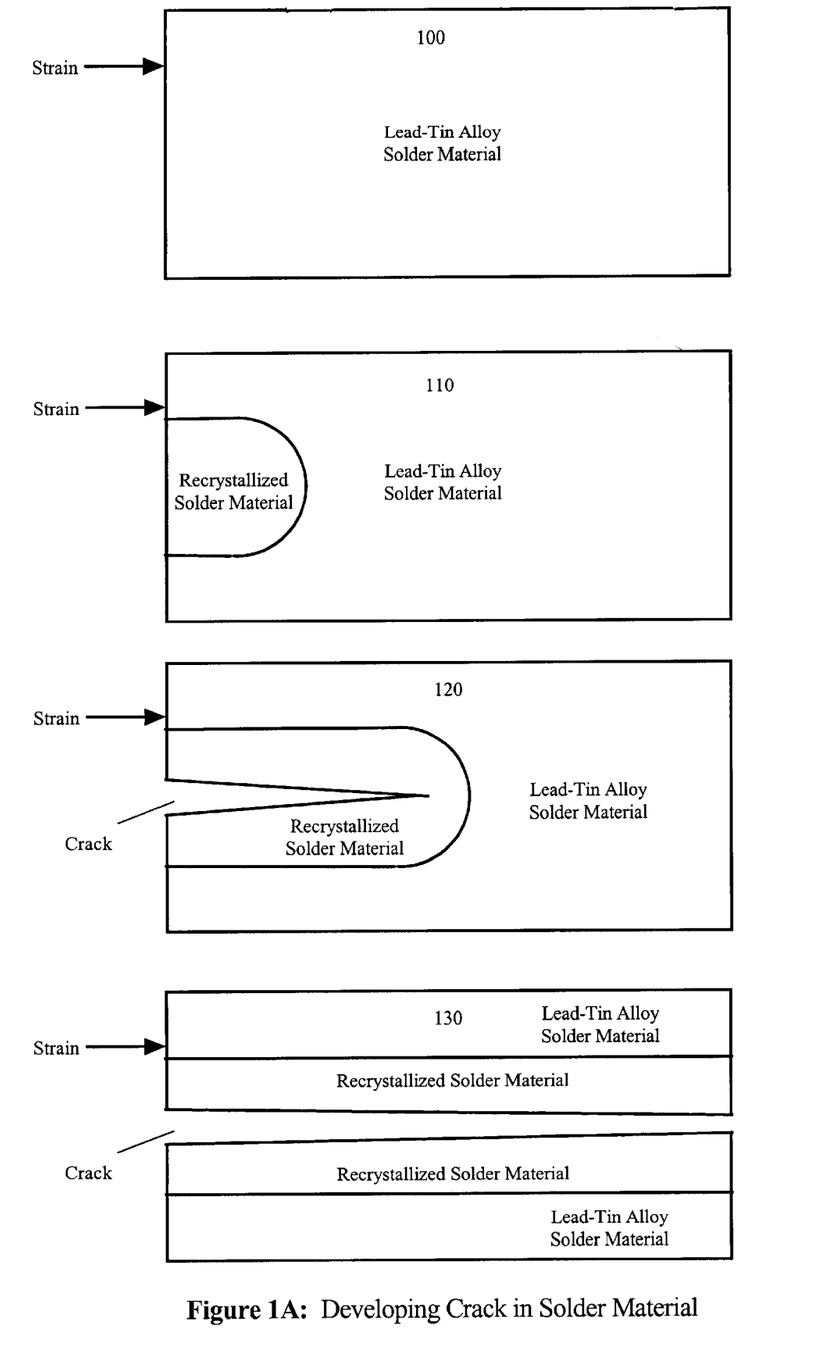
FIG. 1A is a series of block diagrams of a developing crack in a solder joint.

FIG. 1A illustrates a developing crack in a solder joint. At block 100, a strain is applied to a lead-tin alloy solder joint. At block 110, a region of recrystallized solder material appears. At block 120, the region of recrystallized solder material grows and a crack develops. At block 130, both the recrystallized solder material and the crack have spread across the entire solder joint, resulting in a solder joint failure.

Solder Joint Integrity Characterization

Electronic systems (e.g. general purpose computers) typically utilize a circuit board to couple electronic components of the system. A circuit board is comprised of circuitry printed on a firm planar surface. Soldered connections serve both to mechanically affix the components to the circuit board and to electronically couple components to the circuit board circuitry. Communications between these components travel through circuit networks contained on the circuit board. The soldered connections are made simultaneously on many electronic systems which are assembled on high-speed, automated production lines. The components of the electronic system are frequently soldered directly onto the circuit boards rather than to wire leads.

The reliability of solder joints is an important factor in the durability and design of electronic packages. However, advances in electronic technologies driven by the desire for miniaturization and increased circuit speed result in severe operating conditions for the solder joint and thus solder joint reliability problems. Specifically, the mismatched thermal expansion characteristics of the materials joined by the solder and the cyclic temperature fluctuations normally encountered during service constitute a condition of thermal fatigue for the constrained solder.

If the solder joints fail by physically breaking off the components, the entire electronic system may fail to perform properly. Thus, it is desirable to test and rate the mechanical strength of the solder joints. However, solder joint performance predicted by current methods of characterizing solder joint integrity fails to match actual solder joint performance. Prior art methods for characterizing solder joint integrity include shear tests, cold tensile tests and hot tensile tests. These methods are discussed in detail below.

Figure 1B:
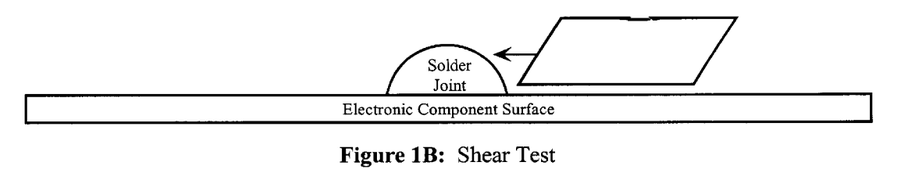
FIG. 1B is a block diagram of a solder joint shear test.

FIG. 1B illustrates a shear test of a solderjoint. A constant rate of strain is applied to the solderjoint by a device from the side. The response force from the solder joint is measured using a force transducer. The response force is monitored until the solder joint fails. Prior art methods record the peak force generated in response to the continuously applied strain. This peak force is used to characterize the integrity of the solder joint and is meant to represent how well the solder joint withstands forces applied to it from the side.

Figure 2:
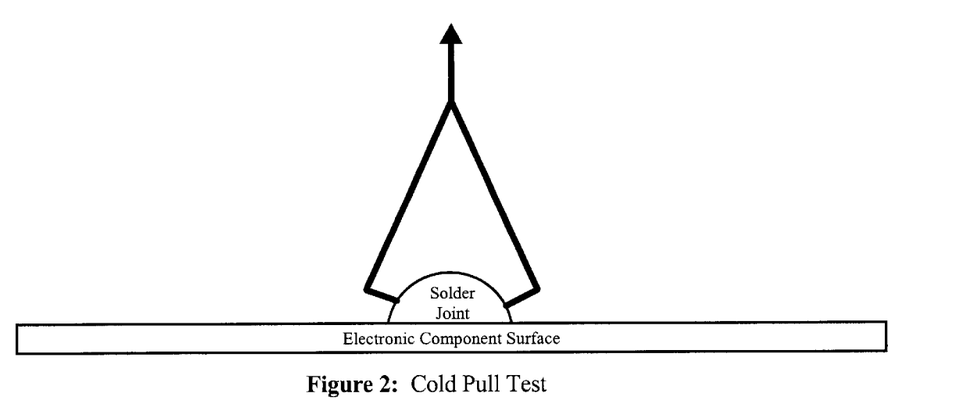
FIG. 2 is a block diagram of a solder joint cold pull test.

FIG. 2 illustrates a cold pull test of a solder joint. A device grips the solder joint and applies a constant rate of strain to the solder joint, pulling it away from the circuit board. The response force from the solder joint is measured using a force transducer. The response force is monitored until the solder joint fails. Prior art methods record the peak force generated in response to the continuously applied strain. This peak force is used to characterize the integrity of the solder joint and is meant to represent how well the solder joint withstands forces which pull it away from the component surface.

Figure 3:
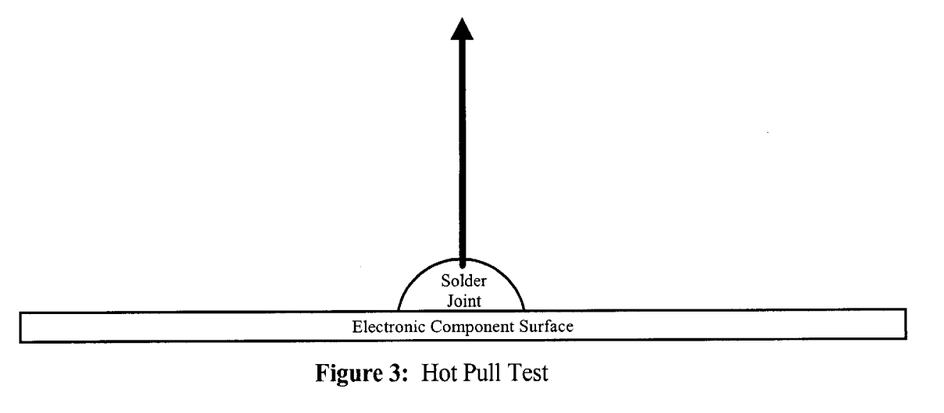
FIG. 3 is a block diagram of a solder joint hot pull test.

FIG. 3 illustrates a hot pull test of a solder joint. A device is heated so that the solder joint partially melts and attaches to the device. Then, a constant rate of strain is applied to the solder joint, pulling it away from the circuit board. The response force from the solder joint is measured using a force transducer. The response force is monitored until the solder joint fails. Prior art methods record the peak force generated in response to the continuously applied strain. This peak force is used to characterize the integrity of the solder joint and is meant to represent how well the solder joint withstands forces which pull it away from the component surface. However, since the hot tensile test requires melting, and thus physically changing, part of the solder joint, reliability of this test is in doubt.

The failed solder joints which occur during circuit board assembly, testing, handling and field use do not have any relation to the results of the above testing methods because the mechanisms of failure do not directly correspond to simply applying a force either at the side of the solder joint or by pulling the joint away from the board. Rather, the mechanisms of failure for solder joints may comprise many types of destructive forces and each of these forces may affect the solder joint in a more or less destructive manner over time and as the force applied varies. The above characterization methods, therefore, are inadequate.

SUMMARY OF THE INVENTION

The present invention is a method for solder joint integrity assessment. The invention comprises collecting data from one or more solder joint strain tests and characterizing the solder joint integrity using a force-deflection graph to represent the collected data. A force-deflection graph has a force-deflection curve, which is the slope of a line that is formed on a graph which plots a solder joint's response force to an applied strain versus time.

One embodiment of the invention uses the slope of the graph to characterize the integrity of the solder joint. Another embodiment uses the area below the slope of the force-deflection curve on the graph to characterize the integrity of the solder joint.

To generate the force-deflection graph, the invention first applies one or more tests to the solder joint. In one embodiment, a shear test is applied to the solder joint. In another embodiment, a cold pull test is applied to the solder joint. In another embodiment, a hot pull test is applied to the solder joint. In yet another embodiment, some or all of these tests are used to collectively obtain a more accurate characterization of the solder joint with which to generate the force-deflection graph. The present invention provides a characterization of solder joint integrity which more accurately predicts solder joint behavior than prior art methods.

BRIEF DESCRIPTION OF THE DRAWINGS

These and other features, aspects and advantages of the present invention will become better understood with regard to the following description, appended claims and accompanying drawings where:

DETAILED DESCRIPTION OF THE INVENTION

The invention is a method for solder joint integrity assessment. In the following description, numerous specific details are set forth to provide a more thorough description of embodiments of the invention. It will be apparent, however, to one skilled in the art, that the invention may be practiced without these specific details. In other instances, well known features have not been described in detail so as not to obscure the invention.

During manufacture and use of electronic systems, it is desirable to be able to predict failure in different aspects of the system. One of these system aspects is the solder joints which couple some components of the system to the rest of the system. Thus, it is desirable to characterize the integrity of these solder joints so that reliability of that aspect of the electronic system can be accurately predicted. Current methods of solder joint characterization (e.g., peak response force from shear or pull tests) fail to adequately predict actual solder joint behavior during system manufacture and use.

The present invention utilizes data to provide a characterization of solder joint integrity. This data can be generated by any conventional form of solder joint integrity test, which includes shear and pull tests. The invention then utilizes one or more of these different forms of data. Thus, the invention more accurately predicts solder joint performance during manufacture and use because instead of characterizing solder joint integrity by way of peak response force, the present invention gathers a plurality of data and forms a force-deflection graph which characterizes solder joint integrity using the slope and area of the curve generated on the graph.

Figure 4:
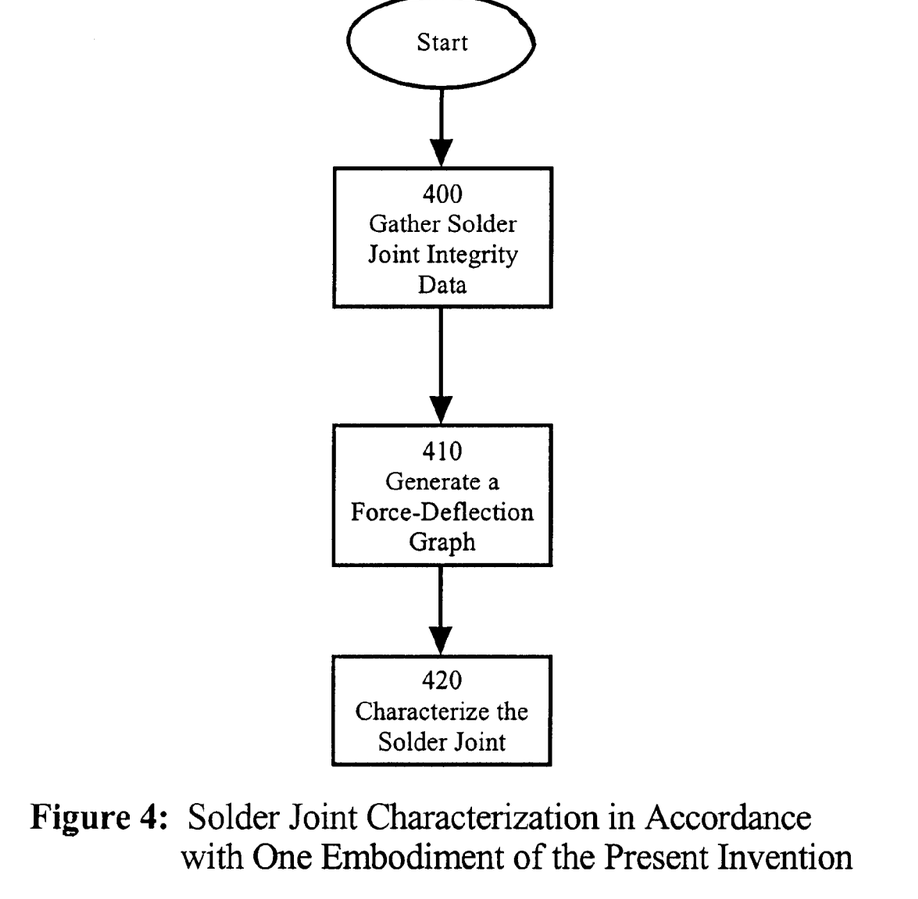
FIG. 4 is a flow diagram of solder joint integrity assessment in accordance with one embodiment of the present invention.

FIG. 4 illustrates the process of one embodiment of the present invention. At step 400, data on the integrity of a solder joint is gathered. At step 410, a plot of the responding force versus time, termed a "force-deflection graph," is generated. Then, at step 420, the force-deflection graph is used to characterize the solder joint.

Solder Joint Integrity Data

Figure 5:
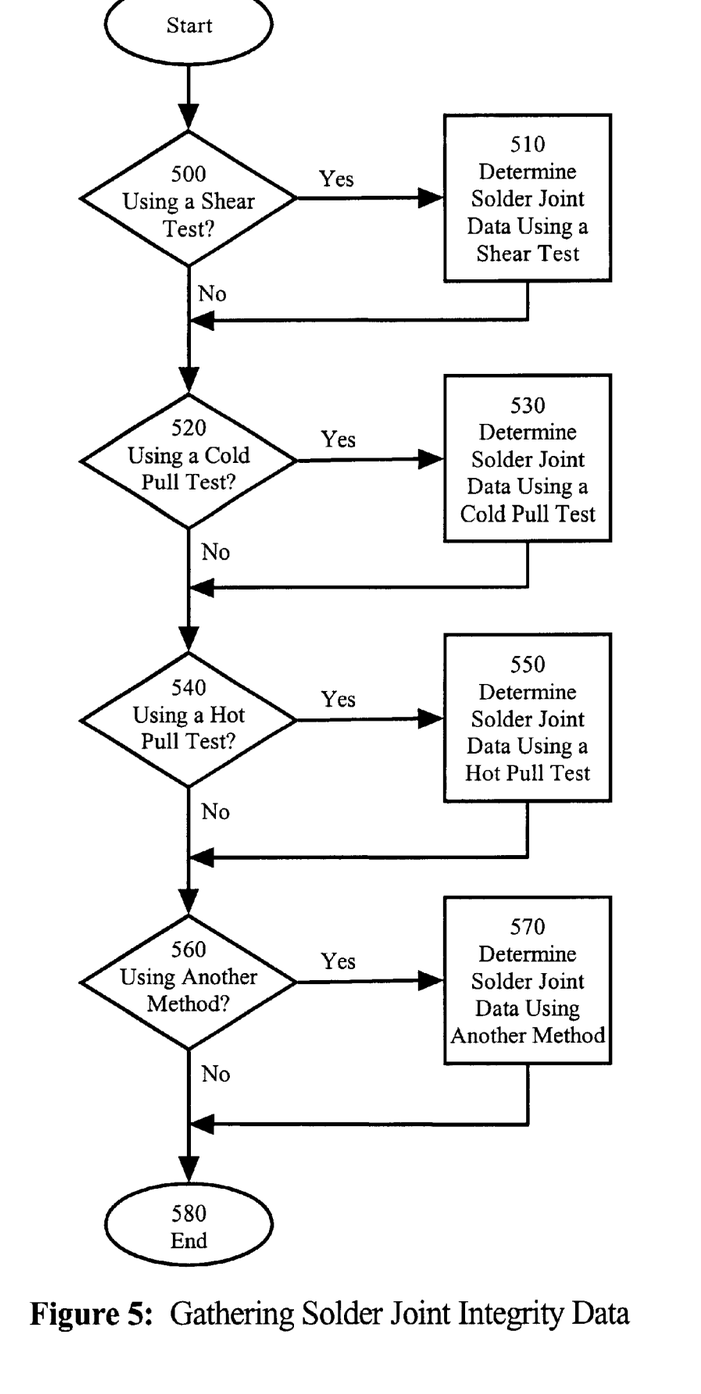
FIG. 5 is a flow diagram of a process for gathering solder joint integrity data in accordance with one embodiment of the present invention.

FIG. 5 illustrates a process for gathering solder joint integrity data in accordance with one embodiment of the present invention. At step 500, it is determined whether a shear test is going to be used as some or all of the solder joint integrity data. If a shear test is to be used, solder joint integrity data is generated using a shear test at step 510. If a shear test is not used or if the shear test solder joint integrity data has already been gathered at step 510, then at step 520, it is determined whether a cold pull test is used. If a cold pull test is used, solder joint integrity data is generated using a cold pull test at step 530. If a cold pull test is not used or if the cold pull test solder joint integrity data has already been gathered at step 530, then at step 540, it is determined whether a hot pull test is used. If a hot pull test is used, solder joint integrity data is generated using a hot pull test at step 550. If a hot pull test is not used or if the hot pull test solder joint integrity data has already been gathered at step 550, then at step 560, it is to be determined if some alternative method is to be used to generate solder joint integrity data. If an alternative method is to be used, solder joint integrity data is generated using the alternative method at step 570. If an alternative method is not used or if the alternative method solder joint integrity data has already been gathered at step 570, then data collection ends at step 580.

Force-Deflection Graph

Figure 6:
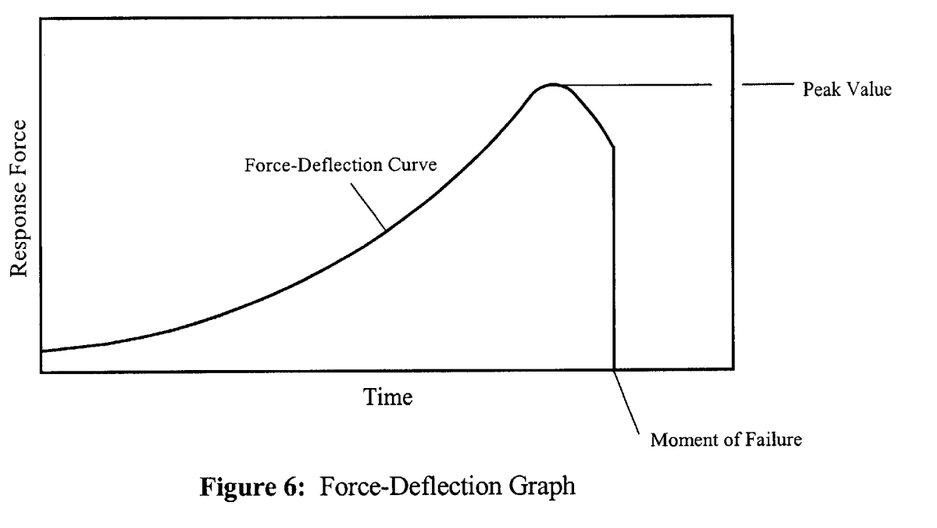
FIG. 6 is a force-deflection graph, in accordance with one embodiment of the present invention.

FIG. 6 illustrates a force-deflection graph. A force-deflection graph is created by applying a strain (e.g., a shearing force) to a solder joint and measuring the response force generated by the solder joint. The response force is plotted against time, resulting in the force-deflection curve indicated in FIG. 6. Typically, this curve grows at some rate to a peak value, for instance, the peak value indicated in FIG. 6. Additionally, the resulting force drops to zero upon failure of the solder joint. Solder joint failure need not occur at the same time the peak response force is reached. In FIG. 6, the response force dropped before the solder joint failed. However, force-deflection curves are not restricted to the type of curve in FIG. 6. A force-deflection curve may be the plot of any continuous function of response force with respect to time.

Figure 7:
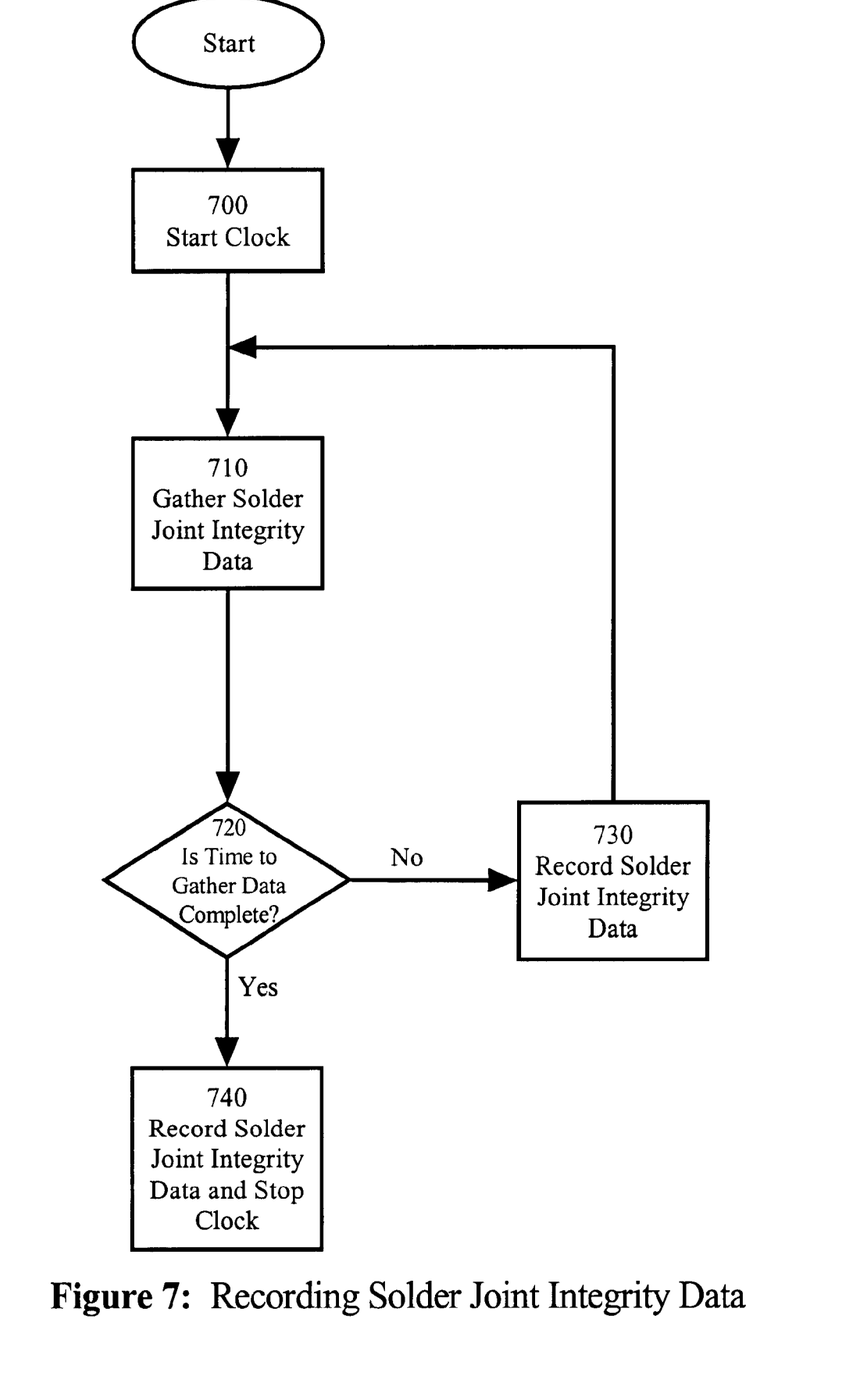
FIG. 7 is a flow diagram of a process for recording solder joint integrity data in accordance with one embodiment of the present invention.

A process for recording a force-deflection curve in accordance with one embodiment of the invention is illustrated by FIG. 7. At step 700, a clock is started. At step 710, solder joint integrity data is collected. Then, at step 720, it is determined whether the time for gathering data is completed. If either a pre-set time limit is reached or the solder joint fails, the solder joint integrity data is recorded and the clock is stopped at step 740. If testing is to continue, at step 730 the solder joint integrity data is recorded and the process moved back to step 710.

The invention characterizes solder joint integrity from the force-deflection graph in two ways: the slope of a curve on the graph and/or the area beneath the curve on the graph. Differences in the slope of the force-deflection curves between solder joints can indicate differences in the joints themselves (e.g., development of cracks, imperfections in solder material or surface irregularities of solder joint).

Figure 8A:
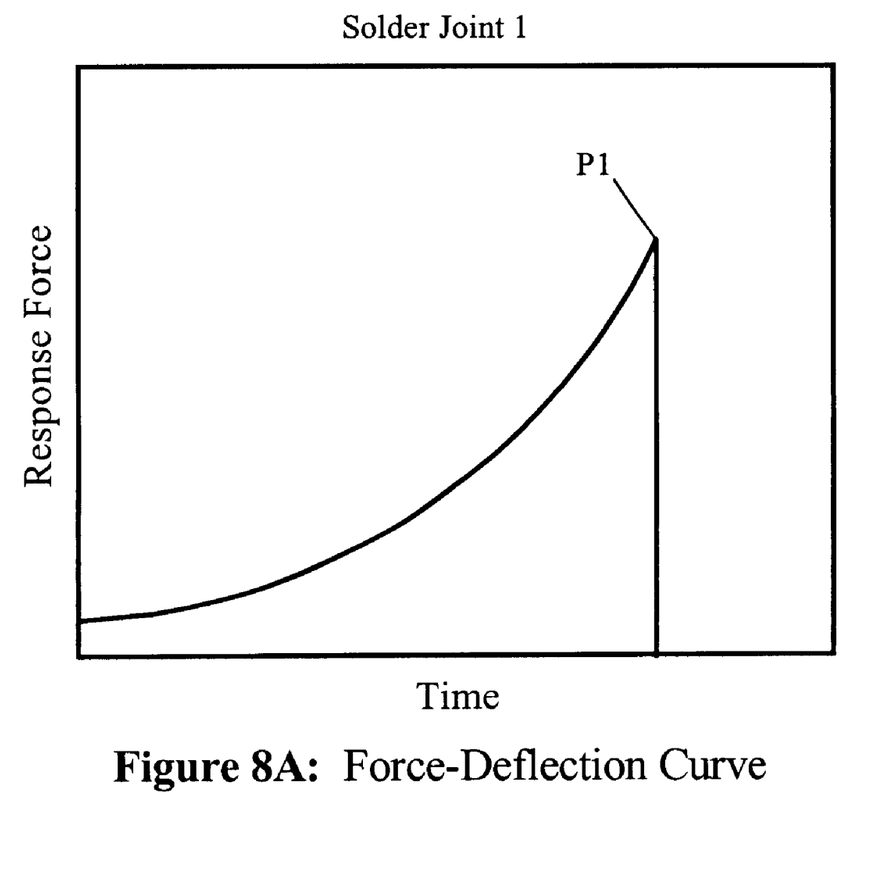
FIG. 8A shows a graph illustrating a force-deflection curve for a solder joint.
Figure 8B:
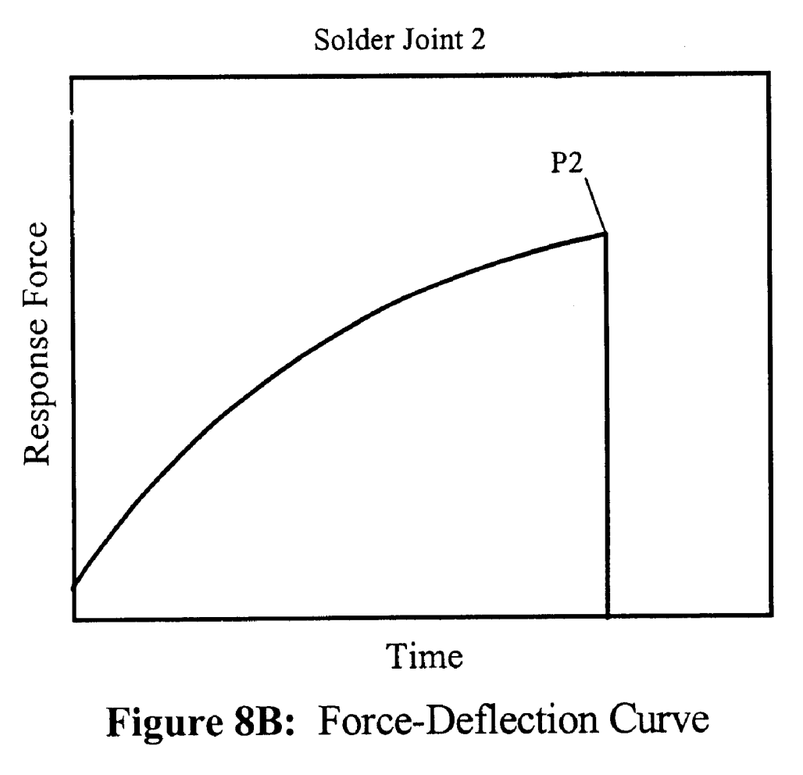
FIG. 8B shows a graph illustrating a force-deflection curve for a solder joint.

FIGS. 8A and 8B illustrate possible force-deflection curves for two different solder joints. Both curves have the same peak resulting force value, indicated as P1 and P2 respectively in FIGS. 8A and 8B. Thus, both solder joints would be characterized as having the same integrity with prior art methods. However, the present invention characterizes these two solder joints differently by using the slope of the force-deflection curve. Since the slope of the two curves are different, the two solder joints are characterized as having different integrities by the present invention.

The present invention also characterizes the integrity of the solder joint using the area beneath the force-deflection curve. The area beneath the curve corresponds to the energy stored within the solder joint during the strain test. Thus, a solder joint with more area beneath the force-deflection curve is characterized as stronger than a solder joint with less area beneath the force-deflection curve.

Figure 8C:
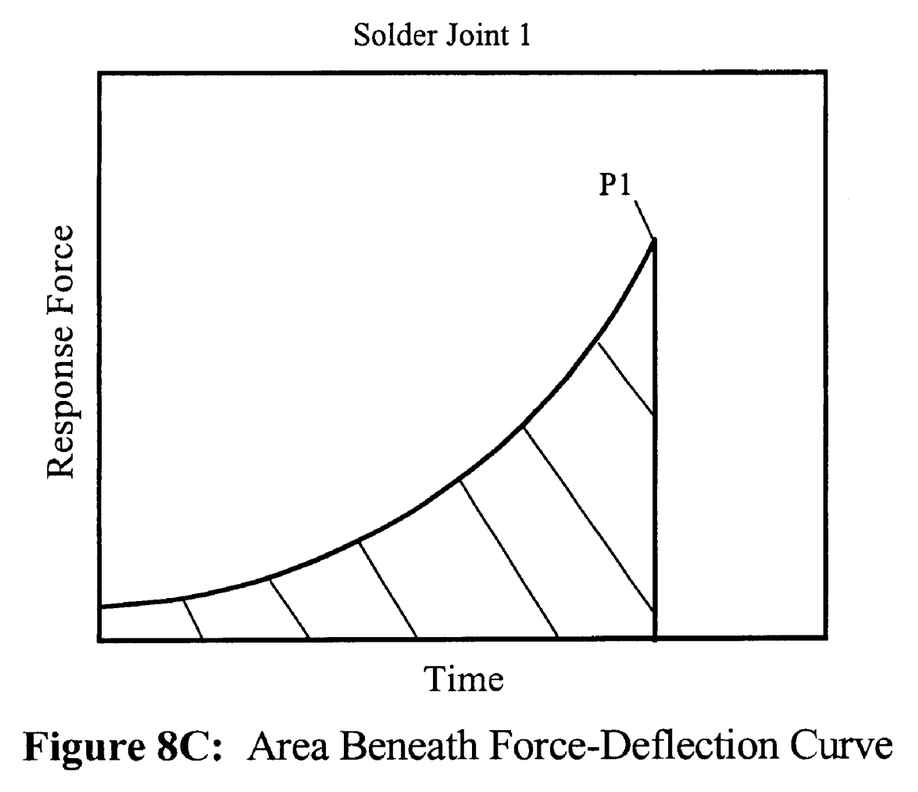
FIG. 8C shows a graph illustrating the area beneath a force-deflection curve for a solder joint.
Figure 8D:
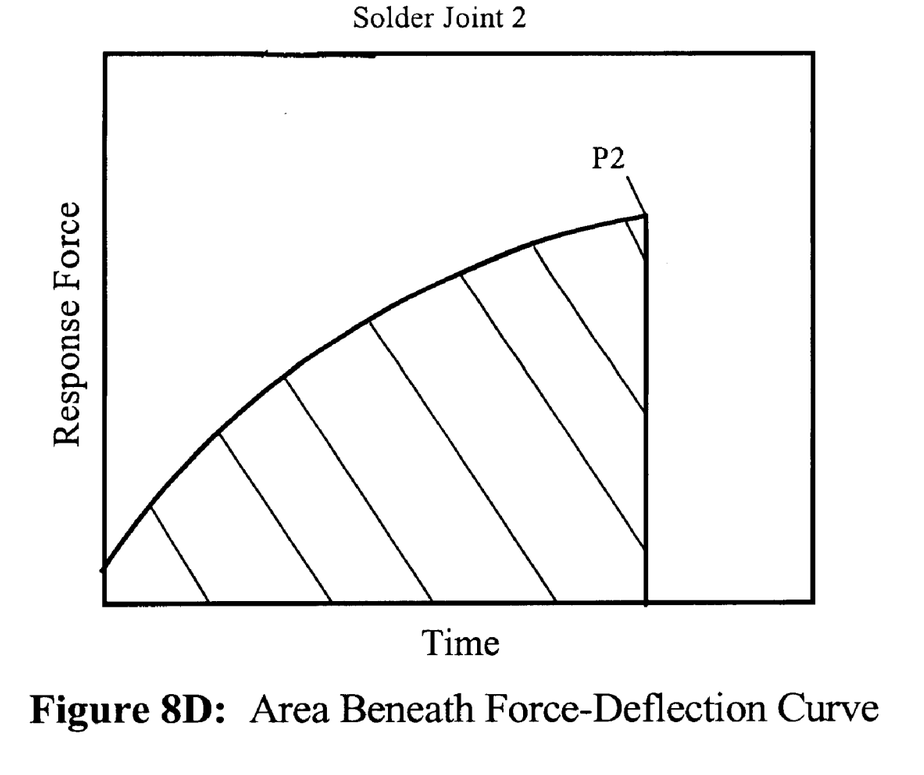
FIG. 8D shows a graph illustrating the area beneath a force-deflection curve for a solder joint.

FIGS. 8C and 8D illustrate the area beneath possible force-deflection curves for two solder joints. The peak response forces, indicated as P1 and P2 respectively in FIGS. 8C and 8D, are the same for both solder joints. Thus, prior art methods characterize the integrity of the solder joints as the same. However, the area beneath the force-deflection curve for solder joint 1 is less than the area beneath the force-deflection curve for solder joint 2. Thus, the two solder joints are characterized as having different integrities.

Solder Joint Integrity Characterization

Figure 9:
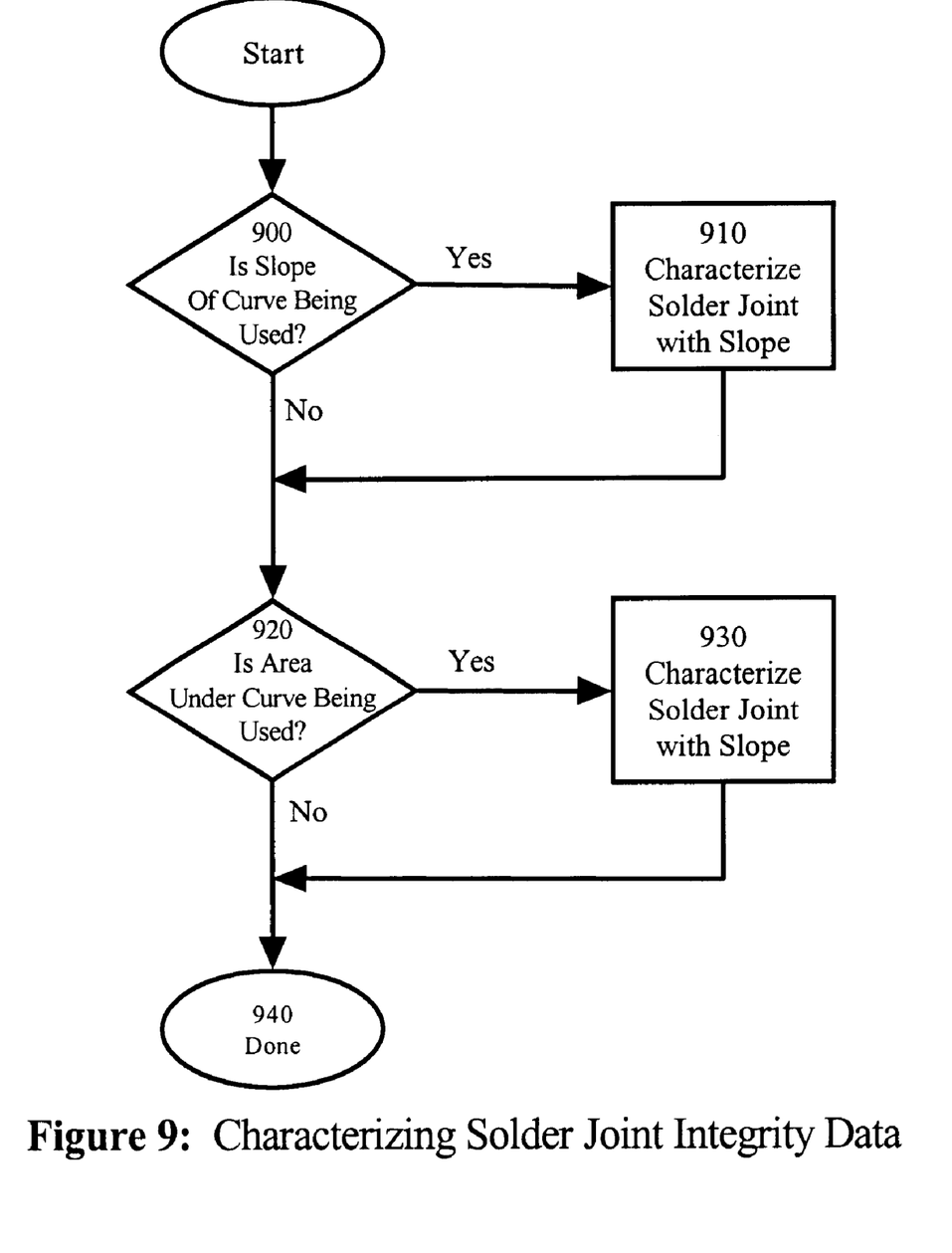
FIG. 9 is a flow diagram of a process for characterizing solder joint integrity data in accordance with one embodiment of the present invention.

FIG. 9 illustrates a process for characterizing solder joint integrity from collected data in accordance with one embodiment of the invention. At step 900, it is determined whether the slope of the force-deflection graph is used to characterize the solder joint integrity. If the slope is used, the solder joint integrity is characterized using the slope of the force-deflection curve at step 910 and the process moves to step 920. If step 900 determines that the slope is not used, the process moves to step 920. At step 920, it is determined whether the area under the force-deflection curve is used to characterize the solder joint integrity. If the area is used, the solder joint integrity is characterized using the area beneath the force-deflection curve at step 930 and the process is complete. Otherwise, the process is complete after step 920.

The present invention's characterization of solder joints corresponds more accurately to solder joint behavior during manufacture and use of electronic systems. Thus, the present invention is an improvement over prior art methods of characterizing solder joint integrity.

Embodiment of Computer Execution Environment (Hardware)

Figure 1C:
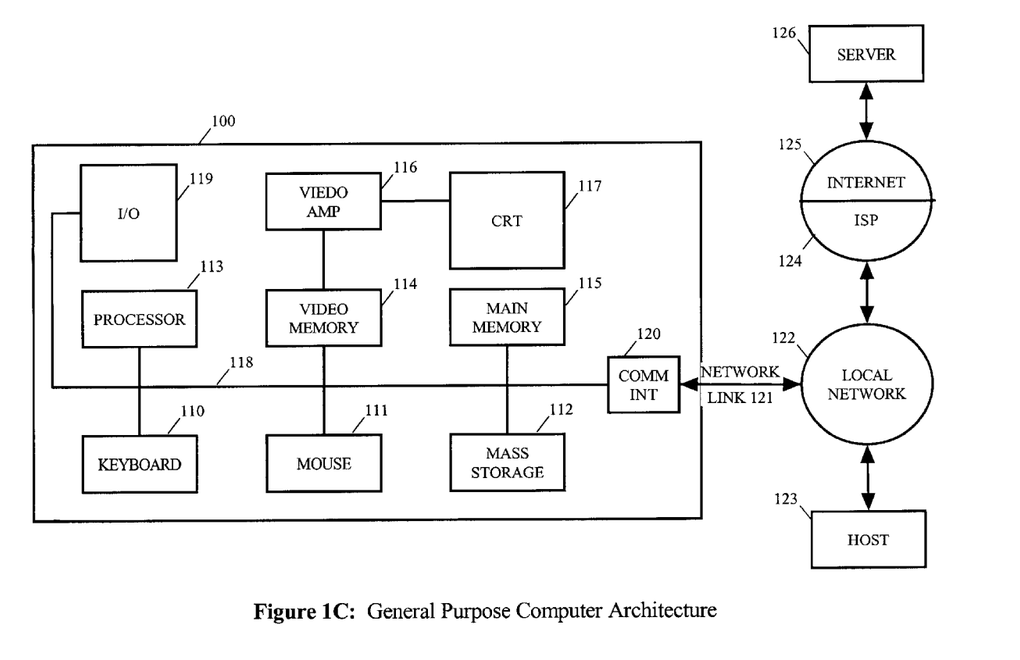
FIG. 1C is a block diagram of a general purpose computer architecture.

An embodiment of the invention can be implemented as computer software in the form of computer readable code executed on a general purpose computer such as computer 100 illustrated in FIG. 1C, or in the form of bytecode class files running on such a computer. A keyboard 110 and mouse 111 are coupled to a bi-directional system bus 118. The keyboard and mouse are for introducing user input to the computer system and communicating that user input to processor 113. Other suitable input devices may be used in addition to, or in place of, the mouse 111 and keyboard 110. I/O (input/output) unit 119 coupled to bi-directional system bus 118 represents such I/O elements as a printer, A/V (audio/video) I/O, etc.

Computer 100 includes a video memory 114, main memory 115 and mass storage 112, all coupled to bi-directional system bus 118 along with keyboard 110, mouse 111 and processor 113. The mass storage 112 may include both fixed and removable media, such as magnetic, optical or magnetic optical storage systems or any other available mass storage technology. Bus 118 may contain, for example, thirty-two address lines for addressing video memory 114 or main memory 115. The system bus 118 also includes, for example, a 32-bit data bus for transferring data between and among the components, such as processor 113, main memory 115, video memory 114 and mass storage 112. Alternatively, multiplex data/address lines may be used instead of separate data and address lines.

In one embodiment of the invention, the processor 113 is a SPARC microprocessor from Sun Microsystems, Inc., a microprocessor manufactured by Motorola, such as the 680X0 processor or a microprocessor manufactured by Intel, such as the 80X86, or Pentium processor. However, any other suitable microprocessor or microcomputer may be utilized. Main memory 115 is comprised of dynamic random access memory (DRAM). Video memory 114 is a dual-ported video random access memory. One port of the video memory 114 is coupled to video amplifier 116. The video amplifier 116 is used to drive the cathode ray tube (CRT) raster monitor 117. Video amplifier 116 is well known in the art and may be implemented by any suitable apparatus. This circuitry converts pixel data stored in video memory 114 to a raster signal suitable for use by monitor 117. Monitor 117 is a type of monitor suitable for displaying graphic images.

Computer 100 may also include a communication interface 120 coupled to bus 118. Communication interface 120 provides a two-way data communication coupling via a network link 121 to a local network 122. For example, if communication interface 120 is an integrated services digital network (ISDN) card or a modem, communication interface 120 provides a data communication connection to the corresponding type of telephone line, which comprises part of network link 121. If communication interface 120 is a local area network (LAN) card, communication interface 120 provides a data communication connection via network link 121 to a compatible LAN. Wireless links are also possible. In any such implementation, communication interface 120 sends and receives electrical, electromagnetic or optical signals which carry digital data streams representing various types of information.

Network link 121 typically provides data communication through one or more networks to other data devices. For example, network link 121 may provide a connection through local network 122 to local server computer 123 or to data equipment operated by an Internet Service Provider (ISP) 124. ISP 124 in turn provides data communication services through the world wide packet data communication network now commonly referred to as the "Internet" 125. Local network 122 and Internet 125 both use electrical, electromagnetic or optical signals which carry digital data streams. The signals through the various networks and the signals on network link 121 and through communication interface 120, which carry the digital data to and from computer 100, are exemplary forms of carrier waves transporting the information.

Computer 100 can send messages and receive data, including program code, through the network(s), network link 121, and communication interface 120. In the Internet example, remote server computer 126 might transmit a requested code for an application program through Internet 125, ISP 124, local network 122 and communication interface 120.

The received code may be executed by processor 113 as it is received, and/or stored in mass storage 112, or other non-volatile storage for later execution. In this manner, computer 100 may obtain application code in the form of a carrier wave.

Application code may be embodied in any form of computer program product. A computer program product comprises a medium configured to store or transport computer readable code, or in which computer readable code may be embedded. Some examples of computer program products are CD-ROM disks, ROM cards, floppy disks, magnetic tapes, computer hard drives, servers on a network, and carrier waves.

The computer systems described above are for purposes of example only. An embodiment of the invention may be implemented in any type of computer system or programming or processing environment.

Thus, a method and apparatus for solder joint integrity assessment is described in conjunction with one or more specific embodiments. The invention is defined by the following claims and their full scope an equivalents.

What is claimed is:

1. A method for characterizing a solder joint comprising:

performing a test on said solder joint; and characterizing said solder joint using said test, wherein said characterizing step comprises:

generating a force deflection graph representing said test.

2. The method of claim 1, wherein said test is a strain test.

3. The method of claim 1, wherein said test is a shear test.

4. The method of claim 1, wherein said test is a cold pull test.

5. The method of claim 1, wherein said test is a hot pull test.

6. The method of claim 1, further comprising analyzing a slope of a curve on said graph.

7. The method of claim 1, further comprising analyzing an area beneath a curve on said graph.

* * * * *